US00PP12366P2

(12) United States Plant Patent
Utecht

(10) Patent No.: US PP12,366 P2
(45) Date of Patent: Jan. 22, 2002

(54) GERANIUM PLANT NAMED 'FISBELLA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,664

(22) Filed: Aug. 3, 2000

(51) Int. Cl.[7] ..... A01H 5/00
(52) U.S. Cl. ..... Plt./332
(58) Field of Search ..... Plt./332, 324

(56) References Cited

PUBLICATIONS

GTITM UPOVROM Citation for 'Fisbella' as per QZ PBR 980831; Jun. 15, 1998.*
2001 Fischer–Schmüllung Plant Alliance Catalog featuring 'FISBELLA' on p. 29 (2001).
Swiss Application for 'FISBELLA'.
European Union Application for 'FISBELLA'.
German Application for 'FISBELLA'.
German Grant for 'FISBELLA'.
Canadian Application, Denomination, Plant Varieties Journal No. 33, Oct. 1999 Canada.#jf139##

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisbella', as described and illustrated, and particularly characterized by the combined features of pink, double flowers, slightly zoned foliage and moderately compact, round plant habit.

2 Drawing Sheets

BACKGROUND OF THE INVENTION

The present invention relates to a new and distinct cultivar of geranium plant, botanically known as *Pelargonium peltatum*, and hereinafter referred to by the cultivar name 'Fisbella'.

'Fisbella' is a product of a planned breeding program which had the objective of creating new ivy geranium cultivars with pink flower color and double-flower form in combination with a well-branched and medium-tall plant habit.

'Fisbella' originated from a hybridization made by the inventor, Angelika Utecht, in a controlled breeding program in Galdar, Gran Canaria, Spain in 1992. The female parent was a hybrid seedling, designated no. 2203/5 (unpatented), characterized by salmon-pink, double flowers. The female parent was derived from crosses between the commercial, unpatented varieties 'Lachskönigin (Salmon Queen)', 'Amethyst', 'Rigi', and 'Pelenberger'. The male parent of 'Fisbella' was the variety 'Fisam' (U.S. Plant Pat. No. 8,327), characterized by light-violet, double flowers, zoned foliage and moderately vigorous growth.

'Fisbella' was selected as one flowering plant within the progeny of the stated cross by the inventor, Angelika Utecht, in 1993 in a controlled environment in Galdar, Gran Canaria, Spain.

The first act of asexual reproduction of 'Fisbella' was accomplished when vegetative cuttings were taken from the initial selection in autumn 1993 in a controlled environment in Galdar, Gran Canaria, Spain, by, or under the supervision of, Angelika Utecht.

Horticultural examination of plants grown from these cuttings, initiated in May 1994 in Hillscheid, Germany, and continuing thereafter, has demonstrated that the combination of characteristics as herein disclosed for 'Fisbella' are firmly fixed and are retained through successive generations of asexual reproduction.

BRIEF DESCRIPTION OF THE INVENTION

The following traits have been repeatedly observed and are determined to be basic characteristics of 'Fisbella', which in combination distinguish this geranium as a new and distinct cultivar:

1. Uniform pink, round, double flowers;
2. Semi-spherically shaped inflorescences;
3. Medium-green foliage with slight zonation;
4. Relatively compact, round and bushy plant habit; and
5. Mid-season spring flowering response.

'Fisbella' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisbella' is the variety 'Fisopa' (U.S. Plant Pat. No. 8,304). In comparison to 'Fisopa', 'Fisbella' has similarly pink-colored flowers, which are more round in shape and contain more petals. The flowers of 'Fisbella' appear to have no markings because the colored veins are most often covered by the inner petals and are therefore not visible. Furthermore, 'Fisbella' has a more compact plant habit, and differently shaped, somewhat larger leaves with weak zonation, in contrast to the foliage of 'Fisopa' which is unmarked and without zonation.

BRIEF DESCRIPTION OF THE DRAWINGS

The accompanying photographic illustrations show typical flower and foliage characteristics of 'Fisbella' with colors being as true as possible with illustrations of this type.

Sheet 1 is a side view of a 'Fisbella' plant in a hanging basket.

Sheet 2 is a close-up view of the inflorescences, buds and leaves.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium peltatum L'Hérit.*

*Commercial.*—Ivy geranium, cv. 'Fisbella'.

Inflorescence:

*Type.*—Umbel. Shape: Semi-spherical. Average diameter: 87 mm. Average depth: 42 mm. Peduncle length: 119 mm. Peduncle color: Light to medium-green, RHS 143 C. Pedicel length: 26 mm (no spur present). Pedicel color: Green, RHS 137 D, no anthocyanin. Number of flowers per umbel: About 6–8. Lastingness of the umbel: Approximately 13 days at 18° C.

*Corolla.*—Average diameter: 57 mm. Form: Double. Shape: Nearly round. Number of petals: About 24. Size of petals: Upper petals 31–33 mm long, 15–17 mm wide; lower petals approximately 25–27 mm long, 15–17 mm wide. Shape of petals: Spatulate, lower petals spatulate to narrow obovate; attenuate base, upper end is truncate or rounded; margin entire, occasionally at the apex slightly dentate. Color (general tonality from a distance of three meters): Uniform light-pink, may fade somewhat to approximately RHS 65 A, when flowers mature. Color of upper petals: RHS 67 D, inner petals near RHS 61 D. Markings of upper petals: Dark-violet veins, RHS 61 A and often with a small dot, RHS 61 A. Color of lower petals: RHS 67 D. Markings on lower petals: Usually absent. Color of lower surface of petals: Color variable between RHS 68 B–RHS 68 C, marbled, with purple-violet veins, near RHS 60 A. Color of sepals: Outer surface light green, RHS 143 C; inner surface RHS 143 C. Number of sepals: 5, occasionally 6. Size of sepals: 13–14 mm long, 5 mm wide for the largest, upper sepal, 3 mm wide for other sepals. Shape of sepals: Linear to lanceolate, acute tip, base truncate, surface weak with pubescence, margin entire.

*Bud (just before petals unfold).*—Shape: Elliptical. Color (sepals): Medium-green, RHS 137 D. Color (petals): Pink to light pink, variable between RHS 68 B, RHS 68 D, and RHS 61 D, and white, marbled. Length: 17 mm. Width: 12 mm.

*Reproductive organs.*—Androecium: Often only 1–2 fertile anthers with white filaments and yellow-orange pollen, RHS 30 A, little pollen produced; additionally 2–4 petaloids, which are mostly infertile. Gynoecium: 5–6 lobed purple stigma and white to pink filament; one pistil per flower. Fertility/seed set: No spontaneous seed set observed.

*Spring flowering response period.*—In Hillscheid, Germany, in 1999, plants had on average 0.6 flowers opened 12 weeks after planting of unrooted cuttings.

*Outdoor flower production.*—Floriferous, the flower count in 1999, in Hillscheid, Germany, indicated about 5.0 inflorescences per plant in mid-May.

*Durability.*—Good shatter resistance and fair to average rain resistance.

*Lastingness of the individual bloom.*—Approximately 7–8 days at 18° C.

*Fragrance.*—None.

Plant:

*Foliage.*—Shape: Ivy-shaped with medium expression of lobes slightly overlapping; cordate base; rounded apex. Margin: Entire, apart from the lobes. Texture: Upper surface is smooth and slightly glossy. Size of leaf: 80 mm wide, 43 mm long. Color of upper surface: Light to medium-green, approximately RHS 137 D. Color of lower surface: Light-green, near RHS 143 B. Color of zonation: Brown, about RHS 166 A; weak, may almost disappear in summer, except on younger leaves. Petioles: 30–40 mm long, 2–2.5 mm in diameter; light green color, approximately RHS 143 C.

*General appearance and form.*—Internode length: 35–45 mm. Branching pattern: 10.1 branches. Size of plant/Length of branches: 18.2 cm (12 week after planting), as measured from the top of the soil (from the base of the main stem) to the tips of the branches, 65–75 cm (in early September, 30 weeks from planting).

Disease/pest resistance/susceptibility: None observed to date.

I claim:

1. A new and distinct cultivar of geranium plant named 'Fisbella', as described and illustrated.

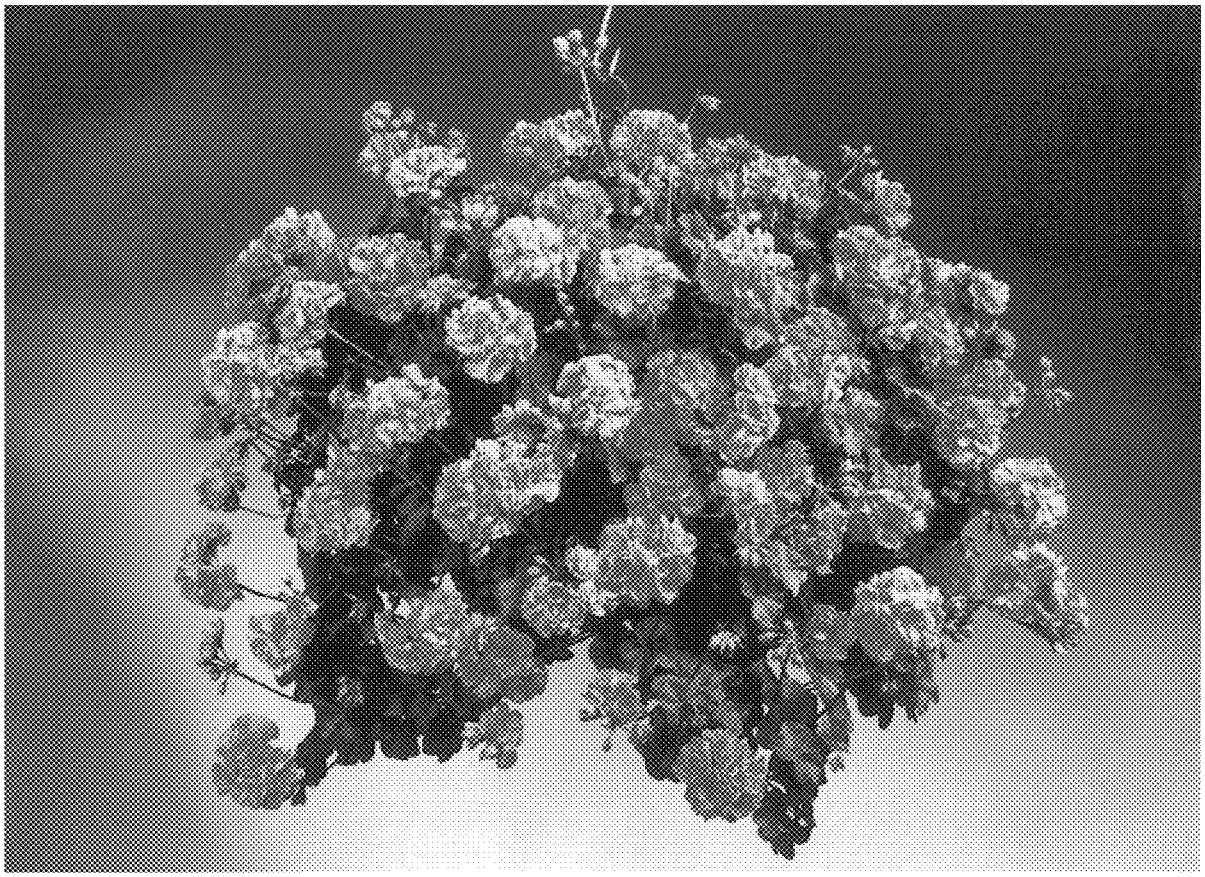

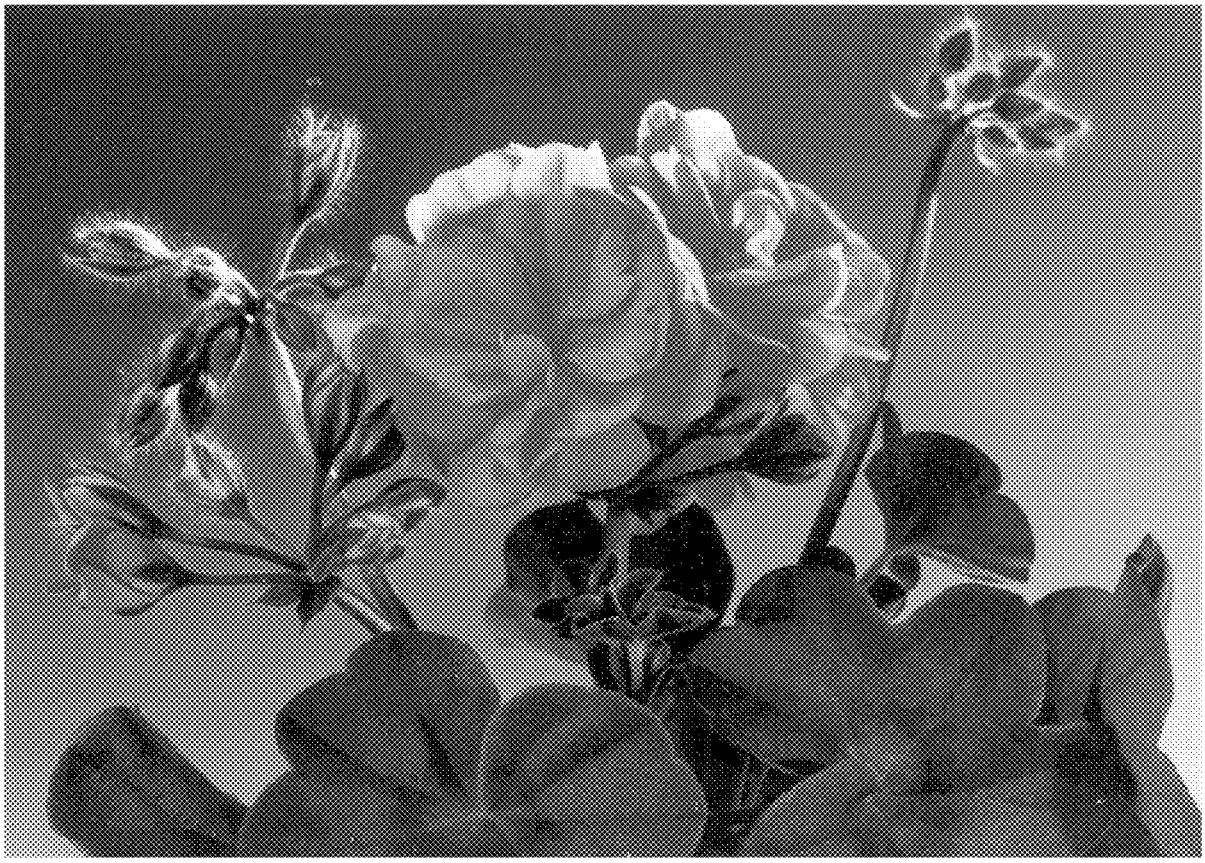

* * * * *